United States Patent [19]

Sipos

[11] Patent Number: 5,433,952
[45] Date of Patent: Jul. 18, 1995

[54] INTRAORAL MEDICAMENT-RELEASING DEVICE

[75] Inventor: Tibor Sipos, Lebanon, N.J.

[73] Assignee: Digestive Care Inc., Lebanon, N.J.

[21] Appl. No.: 109,632

[22] Filed: Aug. 20, 1993

Related U.S. Application Data

[63] Continuation-in-part of Ser. No. 878,155, May 4, 1992, abandoned.

[51] Int. Cl.6 ................................................. A61K 9/14
[52] U.S. Cl. ..................................... 424/489; 424/422; 424/424; 424/435; 424/486; 424/451
[58] Field of Search ................. 424/489, 490, 435, 493

[56] References Cited

U.S. PATENT DOCUMENTS

| | | | |
|---|---|---|---|
| 3,624,909 | 12/1971 | Greenberg | 433/80 |
| 3,688,406 | 9/1972 | Porter et al. | 433/217.1 |
| 4,020,558 | 5/1977 | Cournut et al. | 433/80 |
| 4,175,326 | 11/1979 | Goodson | 433/80 |
| 4,681,544 | 7/1987 | Anthony | 433/215 |
| 4,685,883 | 8/1987 | Jernberg | 433/215 |
| 4,764,377 | 8/1988 | Goodson | 424/435 |
| 4,837,030 | 6/1989 | Valorose, jr. et al. | 424/456 |
| 4,876,092 | 10/1989 | Mizobuchi et al. | 424/435 |
| 4,919,939 | 4/1990 | Baker | 424/493 |
| 4,935,411 | 1/1990 | McNamara | 514/152 |
| 5,011,694 | 4/1991 | Nuernberg et al. | 424/464 |

FOREIGN PATENT DOCUMENTS 0184389 6/1986 European Pat. Off. .

OTHER PUBLICATIONS

M. Friedman, Sustained-Release Delivery System for Treatment of Dental Diseases, Pharmaceutical Reserch, v. 7, No. 4, pp. 313-317, 1990.

D. Mirth et al, Clinical Evaluation of an Introral Device for the Controlled Release of Fluoride, JADA, v. 105, Nov. 1982, pp. 781-797.

H. K. Morisaki et al, Local Ofloxacin Delivery Using a Controlled-Release Insert (PF01) in the Human Periodontal Pocket, J. Periodont. Res. 1990, 25:1:5.

T. Larson, In vitro Release of Doxycycline from Bioabsorbable Materials and Strips, J. Periodontal Research, 1990; 61; 30-34.

M. Friedman, Fluoride Uptake by Powdered Human Enamel Treated with Prolonged Active Fluoride Pellets In Vitro, Arch. Oral. Biol. v. 26, pp.131-134, 1981.

D. Mirth et al, Development and In Vitro Evaluation of an Intra-Oral Controlled-Release Delivery System for Chlorhexidine, J. Dent. Res., Aug. 1989.

Southern Reserch Institute Bulletin, Winter 1979, v. 32, No. 1, pp. 16-22.

*Primary Examiner*—Thurman K. Page
*Assistant Examiner*—William E. Benston, Jr.

[57] ABSTRACT

Disclosed are controlled rate-release devices for releasing a pharmaceutically active agent into the oral cavity by the dissolving action of the saliva, and a method of preparing such devices.

14 Claims, No Drawings

INTRAORAL MEDICAMENT-RELEASING DEVICE

This application is a continuation-in-part of application Ser. No. 07/878,155 filed May 4, 1992, now abandoned.

BACKGROUND OF THE INVENTION

1. Field of the Invention

This invention relates to intraoral medicament-releasing devices capable of slowly releasing an agent into the oral cavity, to a process of manufacturing such devices, and methods for the prevention and treatment of dental caries, incipient carious lesions and periodontal diseases. More particularly, the invention relates to a controlled rate-release device comprising an inner core containing a pharmaceutically acceptable agent and an outer layer of a saliva-insoluble, non-erodible rate-controlling membrane allowing water to enter into the inner core to dissolve the pharmaceutically acceptable agent which then diffuses through the rate-controlling membrane into the oral environment.

2. Reported Developments

Dental practitioners and their patients are aware of the importance of proper oral hygiene in maintaining healthy teeth and gums. Routine use of toothbrush, toothpaste, fluoride rinse and floss as well as periodic visits to the dentist to remove plaque and calculus from the root surfaces greatly contributes to such oral care maintenance. However, this routine must be kept diligently, and even then, it is only effective to a limited extent regarding certain oral conditions.

Dental caries and periodontal diseases are widespread chronic conditions. Caries is an infectious disease caused by bacteria. Bacteria metabolize fermentable carbohydrates to organic acids. The acids in close contact with the enamel cause enamel demineralization. Extensive demineralization leads to dental caries. Caries may be prevented by the frequent use of fluorides. Fluoride enhances enamel remineralization, increases tooth resistance to further acid attack, and arrest the progression of caries. Fluorides are employed in toothpastes, tablets, drops, mouth rinses and drinking water. Periodontal diseases are inflammatory conditions affecting the tooth supporting structures. Anaerobic bacteria proliferates in the gingival crevice, produce enzymes, toxins and noxious metabolites that accumulate in the gingival crevice. These bacterial by-products are irritating to the gingival tissue and initiate a localized inflammation. The inflamed tissues release enzymes that destroy the collagen supporting fibers and alveolar bone. If this process is left unchecked it will eventually lead to the exfoliation of tooth.

In addition to dental caries and periodontal diseases a certain segment of the population suffers from other ailments and conditions of the oral cavity.

Xerostomia, or dry mouth condition, is frequently caused by a dysfunction of the major salivary glands and is associated with a number of diseases. Xerostomia may also be caused by certain medication especially in the elderly. Radiation treatment of head and neck cancer may also result in xerostomia. Patients who undergo orthodontic treatment for various health and cosmetic reasons that require wearing of orthodontic devices experience white-spot enamel lesions around the orthodontic bands due to accumulation of plaque. Denture wearers experience irritation and painful lesions on the roof of the mouth as a result of which masticatory functions are impaired and the patients also develop digestive problems and nutritional deficiencies. Handicapped individuals are at a greater risk of developing rampant caries because of the physical limitations imposed by their handicaps and good oral hygiene.

Periodontal treatment utilizes mechanical debridement of tooth surfaces and root planning and scaling. Systemically administered antibiotics have also shown some promise as an antimicrobial measure.

These treatments, although effective against bacteria at the time of administration are not sufficiently long-lasting. Bacteria proliferates within hours in the oral cavity and condition leading to caries and periodontal disease reappear again. It is apparent that since these disorders are chronic, the duration of drug presence at the target site is critical in both prevention and therapy.

These conditions and ailments are treatable, since it has been shown that a low level of fluoride which constantly enriches the saliva has the potential to prevent the development of dental caries and associated conditions in the oral cavity. (See O. Fejerskov, A. Thylstrup and M. J. Larsen: Rational Use of Fluorides in Caries Prevention. A Concept Based on Possible Cariostatic Mechanisms. Acta Odontol Scand. 39(4): 241–249 (1981)). Accordingly, a fluoride-containing reservoir which can release fluoride at a constant rate to enrich the saliva with therapeutically effective levels of fluoride is required (See D. B. Mirth and W. H. Bowen. A Microbial Aspect of Dental Caries. Vol. 1 pp. 249–262, Information Retrieval Inc., Washington, D.C. (1976)).

It is also apparent that most of the currently marketed products to prevent rampant caries associated with xerostomia and other oral ailments are deficient for several reasons, such as lack of sustained-release fluoride, adequate patient compliance, unpleasant taste and cumbersomeness of application, lack of control of applied dosage and the potential toxic effect from the product being swallowed accidentally.

Although at present there are no commercially available products on the market based on long term sustained-release, controlled delivery principle, efforts are being made to provide such products as illustrated by the following references.

Slow-releasing devices to be attached to or placed around teeth or implanted into the gum are disclosed, for example, in U.S. Pat. Nos. 3,624,909; 3,688,406; 4,020,558; 4,175,326; 4,681,544, 4,685,883, 4,837,030 and 4,919,939. While these devices do deliver a medication into the oral cavity, they lack a controlled rate of delivery for extended time periods which is of utmost importance in the prevention and treatment of the heretofore mentioned diseases and conditions. For example, U.S. Pat. No. 4,837,030 discloses an orally administrable pharmaceutical composition comprising beads coated with an ultrathin layer of a polymer that erodes under gastric conditions. When suspended in water, more than 90% of the pharmaceutical agent is released from the composition between 20 to 90 minutes; U.S. Pat. No. 4,919,939 discloses a controlled release drug delivery system comprising a polymeric matrix which dissolves, releasing the drug contained therein within 10 to 18 hours, upon the action of the saliva.

Polymeric varnishes containing the antiseptic chlorhexidine or cetylpyridinium in ethylcellulose or polyurethane varnishes were found to be effective to prevent plaque formation. However, the antibacterial effects are short-term and the application of the varnishes has to be repeatedly performed by a dentist.

Hollow fibers and methacrylate slabs containing antibacterial agents, such as tetracycline, placed into periodontal pockets were also found effective. Lack of esthetics, pain and discomfort caused by such devices limit their use to only certain patients with extreme cases of periodontal disease.

A device for attachment to teeth and to deliver sodium fluoride or chlorhexidine at a controlled-rate was found effective in delivering the active substances at a constant linear rate. The device comprises a copolymer hydrogel of hydroxyethyl methacrylate and methyl methacrylate as the inner core which holds the active agents, while the outer layer, a copolymer of the same constituents at a different mole ratio controls the drug release rates. See D. B. Mirth et al, Development and In Vitro Evaluation of an Intra-Oral Controlled-Release Delivery System for Chlorhexidine, J. Dent. Res. August (1989); D. B. Mirth et al, Clinical Evaluation of an Intraoral Device for the Controlled Release of Fluoride, JADA, Vol. 105, November (1982).

While this system of delivery is excellent for fluoride and chlorhexidine, there is no process or method disclosed by which the device could be manufactured economically. Laboratory scale or hand-made small size devices of this type tend to be prohibitively expensive and unaffordable by that segment of the public which needs it the most. Also, there is no provision disclosed to tailor-make the device to deliver fluorides or chlorhexidine so that prophylactic or treatment requirements of patients could be satisfied allowing for different rates and duration of delivery. Furthermore, no process is taught by which uniform and predictable dosage could be assured.

The present invention solves these and other problems as will be discussed as the description of the invention proceeds.

SUMMARY OF THE INVENTION

In one aspect, the present invention relates to a controlled rate-release device capable of releasing a pharmaceutically acceptable agent into the oral cavity for a period of thirty to three hundred twenty days and longer, comprising an inner core containing the pharmaceutically acceptable agent therein and an outer layer of a saliva-insoluble, non-erodible rate-controlling membrane allowing water to enter into the inner core to dissolve the pharmaceutically acceptable agent and allowing the creation of an osmotic gradient that forces the solubilized agent to diffuse through the rate-controlling membrane into the oral environment, wherein the inner core comprises of from about 64 to about 84% w/w of a pharmaceutically acceptable active agent; and of from about 35 to about 15% w/w of 2-hydroxyethyl methacrylate/methyl methacrylate co-polymer (hereinafter HEMA:MMA) which comprises of from about 40 to about 60 mole % of HEMA and of from about 60 to about 40 mole % of MMA; and the non-erodible release rate controlling membrane uniformly covering the inner core comprises of from about 20 to about 40 mole % HEMA and from about 60 to about 80 mole % MMA at a coating thickness proportional to the desired rate of release of the active agent from the inner core.

The pharmaceutically active agent utilized in the present invention includes, but is not limited to: fluoride ion releasing substances, such as sodium fluoride, calcium fluoride, amine fluoride, sodium monofluorophosphate and stannous fluoride; antibiotic tetracyclines, such as doxycycline and minocycline (Minocin, Achromycin and Vibramycin); anti-collagenolytic tetracyclines, such as 4,4-dedimethylaminotetracycline; 4-hydroxy-4-dedimethylamino tetracycline, tetracycline-2-hydroxamate and other chemically modified non-antimicrobial tetracycline; anti-microbials, such as chlorhexidine, cetylpyridinium and metronidazole; salivary stimulants, such as pilocarpin; and mouth deodorants, such as alpha and beta ionones.

In another aspect, the present invention relates to a method of preventing/treating dental caries, incipient carious lesions (white spot lesions) around orthodontic appliances in the oral cavity, and preventing/treating periodontal disease.

In a third aspect, the present invention relates to a process of making a slow, controlled rate release device for releasing a pharmaceutically acceptable active agent into the oral cavity.

In the detailed description which follows, the invention will be described with reference to manufacturing sodium fluoride containing controlled-release devices. The preparation of the devices containing active agents other than sodium fluoride, is analogous to that of sodium fluoride-containing devices and should be readily apparent to those skilled in the art.

DETAILED DESCRIPTION OF THE INVENTION

In the preferred aspect, this invention relates to a manufacturing process for making a sodium fluoride releasing matrix tailor-made to slowly release sodium fluoride at a controlled and predictable rate into the oral cavity to prevent tooth decay and the onset of dentinal root caries, said process comprising the steps of:

preparing a core comprising sodium fluoride and HEMA:MMA copolymer; and
coating said core with a membrane forming copolymer of HEMA:MMA.

Preparation of Cores

The fluoride releasing cores are prepared by thoroughly mixing about 64 to 84% w/w, preferably about 74% w/w, of USP grade sodium fluoride and about 35 to 15% w/w, preferably about 25% w/w, of HEMA:MMA copolymer comprising from about 40 mole % to about 60 mole %, HEMA and from about 60 mole % to about 40 mole % MMA, preferably about 50:50 HEMA:MMA in a blender to form a uniform blend of the components. The blend is then granulated by slowly adding a solvent mixture consisting of from about 20% v/v to about 40% v/v and preferably about 30% v/v ethyl acetate and from about 80% v/v to about 60% v/v, preferably about 70% v/v isopropanol, in a suitable mixer to form a granulated paste. The paste is then forced through a 12 mesh standard sieve series stainless steel screen to form uniform granules and dried until the solvent odor is undetectable. The dried granules are then sieved through an 18 mesh screen. Any residual granules remaining on the screen are reduced to less than 18 mesh by grinding in a centrifugal mill. The granules are then blended with USP talc in a ratio of about 95 to 99 parts granules and about 5 to 1 parts talc. The so-obtained homogeneous mixture is then compressed into the desired shapes, such as tablets, capsules, globules, half-football shapes, veneers or thick films.

Compressing is accomplished using a Manesty Beta-tablet press or similar device.

Coating the Cores

In the oral environment the above-described cores would readily release the fluoride content in a relatively short time. Such release of certain oral agents may be desirable, such as an oral anesthetic after oral surgery or for reducing pain due to inflammation of the gums. However, fluoride ions are intended to be released slowly over an extended period of time to prevent coronal and root caries formation. To obtain a product with slow-release characteristics a membrane-forming copolymer-coating is applied onto the cores or matrix.

It was found that the use of HEMA:MMA copolymer provides a coating that allows for essentially tailor-making the duration and degree of slow release ranging from a couple of weeks or less to several months.

The membrane coating of the cores is accomplished using a fluidized bed processing unit, such as the Glatt fluidized bed processing unit equipped with a Wurster insert, as follows:

generating an upward moving high velocity air stream controlled by an air distribution plate located at the bottom of the coating chamber;

placing a partitioning cylinder (Wurster insert) having a top end and a bottom end over said air distribution cylinder and allowing a gap between the bottom of said cylinder and said air distribution plate;

injecting the cores into said high velocity air stream to propel said cores to move upward and separate from each other;

spraying a solution of 30:70 mole % HEMA:MMA co-polymer in a suitable solvent onto the cores being propelled upward;

maintaining an elevated temperature in the high velocity air stream to vaporize the solvent used to dissolve said HEMA:MMA co-polymer and thereby forming a membrane coating of said co-polymer on said cores;

allowing said coated cores to clear the top of said partitioning cylinder and to fall back on the air distribution plate outside said cylinder;

allowing said cores to move through the gap beneath the partitioning cylinder toward the center of the air distribution plate; and allowing said cores to move upward again in said airstream to be coated again until the desired amount of membrane coating is obtained thereon.

The solution of the membrane forming HEMA:MMA co-polymer should be at a concentration of about 1 to 10% w/w, preferably about 3 to 5% w/w HEMA:MMA in a solvent mixture of 4 parts methylene chloride to 1 part isopropyl alcohol.

The percentage of coating applied is determined periodically during the coating process as follows:

$$\% \text{ coating} = \frac{\text{mean core wt. after coating} - \text{mean core weight before coating}}{\text{mean coating weight after coating}} \times 100$$

The process continues until the desired membrane coating levels are obtained, typically 14–18% w/w to release a 0.05 to 0.15 mg/day of fluoride. Other rates are obtainable by applying more or less coating on the cores thereby tailor-making the rate of release to the length of time for slow release desired.

The following examples are intended to further illustrate the present invention without limitation thereof.

EXAMPLE 1

(General Example)

The following solvent mixtures are prepared:
Solvent Mixture A is prepared by mixing
 28.50% v/v ethyl acetate with
 71.50% v/v isopropyl alcohol
Solvent Mixture B is prepared by mixing
 80.00% v/v methylene chloride with
 20.00% v/v isopropyl alcohol.

The desired amounts of powdery ingredients are weighed into separate polyethylene bags and the weights are recorded. The sodium fluoride and the HEMA:MMA 50:50 co-polymer are transferred into a "V" blender and mixed for about five minutes and then discharged into a sigma blender for granulation.

While mixing in the sigma blender, the batch is sprayed with Solvent Mixture A until the batch is sufficiently solvent-wetted for granulation. When the batch is wet enough so that the particles stick together, it is passed through a 12 mesh stainless steel sieve and spread on parchment paper lined trays for drying. The larger lumps which did not pass through the sieve are dried separately and, when sufficiently dry, are broken-up with a centrifugal grinder. When dry, the entire batch is sieved through a 20 mesh sieve and collected in a polyethylene container.

Using the desired shape punches and dyes cores are compressed using the Manesty Beta-press machine. The cores are checked every few minutes during the compressing cycle for weight, hardness and thickness. Adjustment on the running weight can be made on the machine, if so desired. The cores are then collected in a polyethylene container.

The Uniglatt coating machine is primed with Solvent Mixture B prior to starting the coating process. The coating process starts by first recording the average weight of the cores. The cores are then placed in the product container of the Uniglatt machine. The unit is sealed by air pressure and the air flap adjusted to the required fluidization. The changes on the Product Exhaust gauge are continuously monitored to ascertain that there is no co-polymer build-up on the exhaust filter. The proportioning pump delivery rate is set to about 1.5, the spray air pressure is set to about 0.5 bar and the spraying of the fluidized cores is started. The build-up of the co-polymer membrane on the cores is checked about every 15 minutes and recorded. When the desired coating level is achieved the proportioning pump and the spray air pressure is shut-off but the fluidizing is continued for about 20 to 30 minutes to drive off the residual solvent.

The finished product is then discharged form the Uniglatt product container into polyethylene storage containers and the net weight is recorded.

Coating weight is calculated by the following equation:

$$\% \text{ coating weight} = \frac{(X - Y) \times 100}{X}$$

where

X = average weight of coated product
Y = average weight of uncoated products.

EXAMPLE 2

Utilizing the procedure described in general Example 1, the following samples were prepared:

| I. Granulation | % W/W | 2 Kilo Batch (g) |
|---|---|---|
| Sodium fluoride, U.S.P. | 74.25 | 1485.00 |
| HEMA:MMA (50:50) | 24.75 | 495.00 |
| Talc, U.S.P. | 1.00 | 20.00 |
| | 100.00 | 2000.00 |

| II. Cores | mg | mg |
|---|---|---|
| Sodium fluoride, U.S.P. | 61.63 | 38.61 |
| HEMA:MMA (50:50) | 20.54 | 12.87 |
| Talc, U.S.P. | 0.83 | 0.52 |
| | 83.00 | 52.00 |

| III. Coated Cores | mg | % W/W | mg | % W/W |
|---|---|---|---|---|
| Sodium fluoride, U.S.P. | 61.63 | 62.25 | 38.61 | 61.97 |
| HEMA:MMA (50:50) | 20.54 | 20.75 | 12.87 | 20.66 |
| Talc, U.S.P. | 0.83 | 0.84 | 0.52 | 0.84 |
| HEMA:MMA (30:70) | 16.00 | 16.16 | 10.30 | 16.53 |
| | 99.00 | 100.00 | 62.30 | 100.00 |

EXAMPLE 3

The rate of fluoride-release from HEMA:MMA membrane coated sodium fluoride core tablets was evaluated. The tablets consisted of a sodium fluoride containing core coated with a rate-controlling co-polymer membrane. Four samples with varying polymer coating thickness were studied.

The composition of the final 14% co-polymer coated tablet is:

| Core | Sodium Fluoride | 55.99 mg |
|---|---|---|
| | HEMA:MMA (50:50 mole %) | 18.66 |
| | Talc | 0.75 |
| Coating | HEMA:MMA (30:70 mole %) | 12.80 |
| | TOTAL | 88.20 mg |

The specification of the 14% co-polymer coated tablet is:

| NaF Content | 55.99 NaF-25.33 mg F-ion |
|---|---|
| Dimensions in mm | 8.4(l) × 3.4(w) × 2.4(h) |
| Average Weight | 88.1 ± 0.5 mg |
| F-ion Release | 0.09 mg per 24 hours |

The core preparation consisted of mixing the 50:50 mole % HEMA:MMA co-polymer with sodium fluoride in a blender. The mixture was granulated to a paste, passed through a sieve to obtain granules. The granules were dried in an oven under a stream of warm and dry air, not exceeding 80° C. and 40% humidity, until all solvents were removed. If residual solvent odor was detected, the granules were dried in a desiccator under vacuum. The granules were reduced in size using a centrifugal grinding mill, and compressed into cores of desired shape.

The release rate-controlling membrane was applied by the method described in Example 1. The coating was composed of 30:70 mole % HEMA:MMA co-polymer and it was applied in four steps. The rate of fluoride release was determined after each coating step.

Standard Test Method

Fluoride release rates from the intraoral fluoride-releasing device (IFRD) were determined as follows:

1. Scope and Purpose
   1.1 This method used to determine the average daily fluoride ($F^-$) release rate from intraoral fluoride-releasing devices (IFRD) designed to passively release controlled (constant) amounts of $F^-$ into the oral cavity for at least six months.

2. Principle of Method
   2.1 An IFRD is placed in a plastic jar and a diffusion buffer solution is added. The jar is mounted in a rotator and the entire apparatus is placed in a thermostated incubator. The diffusion buffer simulates the pH and ionic strength of saliva and contains the major salivary ions (except calcium). The amount of $F^-$ released by the IFRD into the diffusion buffer is assayed potentiometrically with a $F^-$ ion specific electrode and an Orion® 940 Expandable Ion Analyzer or equivalent electrometer.

3. Interferences
   3.1 Due to the inherent reactivity of $F^-$ ion with glass, all $F^-$ solutions were mixed, stored and dispensed from plastic labware.
   3.2 Ionic activity is a function of temperature. Whenever laboratory temperature varied by more than 2° C. from the original standardization conditions, standardization was repeated.
   3.3 Since the $F^-$ ion specific electrode responds to hydroxide ($OH^-$) ion, but does not respond to HF, all $F^-$ measurements were carried out in between pH 5.0 to 5.5 to minimize erroneously high readings due to $OH^-$ ion contribution or to the formation of HF [$Ka_{(HF)} = 3.5 \cdot 10^{-3}$].
   3.4 A total ionic strength adjusting buffer (TISAB-II) Orion® was used in equal proportions with all $F^-$ solutions to provide a constant background ionic strength, to decomplex bound $F^-$ and to adjust solution pH between 5.0 and 5.5.

4. Precision and Accuracy
   4.1 Precision: Measured concentration of $F^-$ is reproducible to ±2% based on repeated (n=10) measurements of one sample.
   4.2 Accuracy: Based on repeated (n=10) measurements of a 5.0 ppm $F^-$ standard solution, the accuracy is ±4%.

5. Reagents
   5.1 Orion® TISAB-II (#940909).
   5.2 Orion® 100±0.5 ppm $F^-$ standard solution (#940907).
   5.3 Orion® 1 ppm $F^-$/TISAB standard solution (#040906).
   5.4 Orion® 10 ppm $F^-$/TISAB standard solution (#040908).
   5.5 Baxter® pH 7.00 calibrating buffer solution (#H7590-7A) or equivalent.
   5.6 Baxter® pH 4.00 calibrating buffer solution (#H7590-7A) or equivalent.
   5.7 Deionized distilled water (DDW)
   5.8 Diffusion buffer stock solution:
      5.8.1 Solution A: dissolve 1.24 g $NaH_2PO_4.H_2O$, 115.13 g KCl and 2.0 g $NaN_3$ in 600 ml DDW.
      5.8.2 Solution B: dissolve 41.98 g 3-(4-morpholino)-propane sulfonic acid [MOPS] in 300 ml water.

5.8.3 Solution B is added to Solution A and pH is adjusted to 7.3 using 50% NaOH (ca. 10 mls). Sufficient water is added to make 1 L.

5.9 Diffusion buffer solution: Prior to use, diffusion buffer stock solution is diluted [5.8.3.] 10-fold (100 ml stock solution diluted with 900 ml DDW) and pH adjusted to 7.0 if required. The diffusion buffer system has a pKa 7.2 with $\Delta pH/°C.=0.006$) and is bactericidal.

6. Standardization
6.1 Unit Performance Check: according to Orion ® manufacturer's manual.
6.2 pH Calibration: according to manufacturer's manual. A two-point calibration with pH 4.00 and 7.00 standard buffers is used.
6.3 $F^-$ Calibration: according to Orion ® manufacturer's manual. A two-point calibration with 1.00 ppm$F^-$ and 10.0 ppm$F^-$ standard solutions is used.
7. Procedure
7.1 IFRD Selection/Inspection: Devices are randomly selected and visually inspected under 10× magnification for defects (obvious cracks or other membrane imperfections) until six satisfactory devices are obtained.
7.2 IFRD $F^-$ Release: Each inspected device is weighed to the nearest 0.1 mg and placed individually into a 120 ml plastic jar which was pre-rinsed with diffusion buffer solution. Jar and lid are labelled with an identifying number. 100 ml of diffusion buffer [5.9.] is added to each jar. Each jar is mounted on the platter of an end-over-end rotator (Fischer Scientific Chemistry Mixer) at using two large rubber bands and the rotator is placed into a thermostated incubator.
7.3 Diffusion Buffer Blank: A diffusion buffer blank jar to correct for the background amount of $F^-$ was prepared by adding 100 ml of diffusion buffer [5.9] to a jar without an IFRD. This jar was mounted with the IFRD sample jars [7.2.].
7.4 IFRD Buffer Change: Jars [7.2., 7.3.] from the incubator were removed on each Monday and Friday and a 10 ml aliquot of each buffer solution was decanted into separate, prelabeled 15 ml plastic tubes for subsequent $F^-$ analysis. The remainder of the diffusion buffer was discarded. 100 ml of fresh diffusion buffer [5.9.] was added to all jars and replaced in the incubator. The diffusion buffer changes were repeated until the $F^-$ release had ceased. Date and time of buffer change were recorded to nearest half hour and rotation (8 rpm) was continued.
7.5 $F^-$ measurements: 2.0 ml of each diffusion buffer aliquot [7.4.] was transferred into a 30 ml plastic cup and 2.0 ml of TISAB solution was added. A magnetic stirring bar was inserted and stirred gently. A previously standardized $F^-$ ion specific electrode was placed into the stirred sample and the $F^-$ concentration (ppm) was measured to the nearest 0.01 ppm $F^-$. When the meter reading was stable, the $F^-$ concentration was recorded. The electrode was rinsed with distilled water and blotted dry with a soft tissue. If the laboratory temperature varied by more than 2° C. from original standardization conditions, the $F^-$ electrode was re-standardized.
8. Calculations
8.1 The total amount (mg) of $F^-$ contained within each jar was calculated by multiplying the meter reading (ppm $F^-$) of each sample aliquot [7.2.] by the volume of diffusion buffer in liters (L). [ppm=mg$F^-$/L]

8.2 The net amount (mg) of $F^-$ released from the IFRD into the diffusion buffer was calculated by subtracting the background amount of $F^-$ from the total amount of $F^-$ present in each sample of diffusion buffer.

8.3 The average daily $F^-$ release rate was calculated as the net amount of $F^-$ released (mg) into the buffer divided by the number of elapsed days between buffer changes. (Rate=mg $F^-$/day).

The fluoride-release rates were found to be proportional to the thickness of the rate-controlling co-polymer membrane. The theoretical release rates and actual results are as follows:

| Coating | Theoretical F-Release/ 24 hr | Theo. Total Release Time | Actual Release 24/hr | Actual F-Release Time | % F Released |
|---|---|---|---|---|---|
| 8% | 0.3 mg | 84 days | 0.27 mg | 86 days | 100 |
| 10% | 0.15 mg | 168 days | 0.135 mg | 164 days | 89 |
| 14% | 0.09 mg | 282 days | 0.10 mg | 260 days | 96 |
| 18% | 0.075 mg | 308 days | 0.07 mg | 320 days | 97 |

EXAMPLE 4

(Comparative Example based on U.S. Pat. No. 4,919,939)

Microspheres were prepared as follows:

Hydrogel particles of methyl methacrylate (MMA) and hydroxyethyl methacrylate (HEMA) containing micronized sodium fluoride were prepared by: dissolving 3 g of the HEMA/MMA co-polymer in a mixture of 25 ml of 60:40 acetone:p-dioxane; suspending 1.0 g of micronized sodium fluoride in the solution; casting a 200 micron thin film onto a glass plate; and drying the film.

Three kinds of samples were prepared from the film:
a) the film as is;
b) the film was ground into particles with an average diameter of 100–200 microns; and
c) the ground film particles were formed into tablets.

The three kinds of samples were tested for fluoride release as described in the Standard Test Method.

The results showed that:
a) the film samples released most of their fluoride content in about 12 to 13 hours;
b) the ground-up film samples released most of their fluoride content in about 9 to 10 hours; and
c) the tableted film samples released most of their fluoride content in about 14 to 15 hours.

EXAMPLE 5

Fluoride release was tested utilizing 14% HEMA/MMA coated NaF tablets of the present invention using the Standard Test Methods. Two sets of samples were tested.

a) One set of samples were immersed in water in beakers, these are the so-called "Unattached" samples, unhindered by any attachment to teeth and all the surfaces of the samples are available for fluoride release.
b) The other set of samples were mounted onto teeth, i.e. "Attached", simulating the actual environment in use in the patients' mouths.

The result showed that:
a) the "Unattached" sampels released most of their fluoride content in about 120 to 140 days; and
b) the "Attached" samples released most of their fluoride content in about 260 to 270 days.

Those skilled in the art will appreciate that other drugs, flavors and pharmaceutically acceptable mouth deodorants in the form of solids or liquids may be incorporated into the slow release device of the present invention. Their rate of release and amount of release can be tailor-made as illustrated in Example 3.

The present invention is also directed to a method of preventing dental caries (enamel and dentinal), development of incipient carious lesions (white spot lesions) around orthodontic appliances in the oral cavity in a mammal by administering an effective amount of $F^-$ to said mammal that is released at a constant rate from the slow, controlled rate-release device which is placed into the oral cavity. Such release should be from about 0.01 to about 0.15 mg/day of $F^-$ from about 80 to about 2530 days.

The invention also provides a method of treating periodontal diseases in a mammal by inhibiting collagenolytic enzyme by releasing from a slow, controlled rate-release device, which is placed into the oral cavity, a collagenolytic enzyme inhibitor at a rate of from about 0.05 to about 1.0 mg/day for 30 to 180 days.

Those skilled in the art of prevention/treatment of dental diseases will appreciate the significance of the above-referred two methods.

As referred to earlier, dental caries is a prevalent disease affecting almost all adults. Caries in patients whose salivary flow has been reduced pose special risks. Radiation therapy to the head and neck for treatment of cancer results in a marked decrease in salivation when the field of radiation includes the major salivary glands. Those with resultant xerostomia can experience a rampant caries rate of 2.5 surfaces per month. If these teeth become badly infected with caries and have to be extracted, the patient is also at risk for osteoradionecrosis, a sometimes fatal disease.

Fluorides have been documented to be effective in reducing caries. Low concentrations of fluoride compounds are provided in water, dentifrices, and mouth rinses. Professionally applied highly concentrated fluoride preparations race available in the dentist's office. For patients with active caries, high concentration home-use fluorides are available by prescription. These home use fluorides have also been shown to prevent caries in xerostomic populations. The typical treatment recommended is to provide the patient with custom made trays. The patient then self-administers approximately 5 ml of a 1.1% NaF (prescription) for 4 minutes daily. This method is cumbersome, messy, can cause gagging and needs 100% compliance on the part of the patient in order to be effective in preventing caries.

There is also concern that daily use of a high fluoride concentration can result in inadvertent ingestion of high doses of $F^-$ that causes fluoride toxicity and the development of gastric ulcers.

Low levels of fluoride work in preventing caries by facilitating the remineralization process while a tooth is exposed to a caries attack. The method of the present invention delivers a daily low dose of fluoride without the problems of complying with a cumbersome regime.

An Intraoral Fluoride Releasing System (IFRS) consisting of a retainer containing a slow-releasing sodium fluoride pellet (IFRD), provides a constant, low level (0.07 mg daily) source of fluoride. After installation of the $F^-$ releasing device into the oral cavity by a dentist, the device releases fluoride automatically and requires no compliance on the part of the patient. These patients will be wearing two IFRD's and, therefore, will be receiving 0.14 mg $F^-$ daily (or 0.31 mg as NaF). There is an abundance of data to show that 0.14 mg $F^-$ daily is non-toxic and non-irritating.

It will also be understood that while the preferred embodiment of the invention has been described, variations may be made thereto without departing from the spirit of the invention.

What is claimed is:

1. A process of making a controlled rate-release device capable of releasing a pharmaceutically acceptable active agent at an essentially constant rate into the oral cavity for a period of about thirty to about three hundred twenty days, said controlled rate-release device comprising:
   (1) a plurality of granules comprising an intimate blend of 2-hydroxyethyl methacrylate/methyl methacrylate copolymer and said pharmaceutically acceptable agent, said plurality of granules compressed together to form a core of said device; and
   (2) an outer layer of a saliva-insoluble, non-erodible rate-controlling membrane encasing said core allowing water to penetrate into said core to solubilize said pharmaceutically acceptable agent and allowing the creation of an osmotic gradient that forces said solubilized agent to diffuse through the rate-controlling membrane at an essentially constant rate into the oral environment, said process comprises:
   (a) preparing a pharmaceutically acceptable agent releasing core by blending about 64 to about 84% w/w of a pharmaceutically acceptable active agent and about 35 to about 15% w/w of 2-hydroxyethyl methacrylate/methyl methacrylate co-polymer which comprises about 40 to about 60 mole % of 2-hydroxyethyl methacrylate and about 60 to about 40 mole % of methyl methacrylate;
   (b) granulating the blend in the presence of a solvent mixture consisting of from about 20 to about 40% v/v of ethyl acetate and from about 80 to about 60% v/v of isopropyl alcohol;
   (c) forming uniform granules from the granulated blend and drying off the solvent;
   (d) blending the dry granules with talc in a ratio of 95 to 99 parts granules and 5 to 1 parts talc;
   (e) compressing the blend into cores; and
   (f) coating said cores to form said rate-controlling membrane by spraying onto said cores a solution of about 1 to about 10% w/w of a membrane forming 30:70 mole % 2-hydroxyethyl methacrylate/methyl methacrylate co-polymer in a solvent mixture of about 4 parts methylene chloride to about 1 part isopropyl alcohol, wherein said rate-controlling membrane constitutes from about 5% w/w to about 20% w/w of the total weight of said controlled rate-release device.

2. The preparative method of claim 1 wherein said pharmaceutically acceptable active agent is selected from the group consisting of sodium fluoride, stanneous fluoride, calcium fluoride, amine fluoride and sodium monofluorophosphate.

3. The preparative process of claim 1 wherein said pharmaceutically acceptable active agent is selected from the group consisting of an antibiotic, an antimicrobial, a salivary stimulant and a mouth deodorant.

4. The preparative process of claim 1 wherein said pharmaceutically acceptable active agent is selected from the group consisting of a tetracycline.

5. The preparative process of claim 1 wherein said core is in the shape of a tablet.

6. The preparative process of claim 1 wherein said core is in the shape of a rod.

7. The preparative process of claim 1 wherein said core is in the shape of a capsule.

8. The preparative process of claim 1 wherein said core is in the shape of a veneer.

9. The preparative process of claim 1 wherein said core is in the shape of a thick film.

10. The preparative process of claim 1 wherein said core is in the shape of a half-football.

11. A process of making a controlled rate-release device capable of releasing a pharmaceutically acceptable active agent at an essentially constant rate into the oral cavity for a period of about thirty to about three hundred twenty days, said controlled rate-release device comprising:

(1) a plurality of granules comprising an intimate blend of 2-hydroxyethyl methacrylate/methyl methacrylate copolymer and said pharmaceutically acceptable agent, said plurality of granules compressed together to form a core of said device; and (2) an outer layer of a saliva-insoluble, non-erodible rate-controlling membrane encasing said core allowing water to penetrate into said core to solubilize said pharmaceutically acceptable agent and allowing the creation of an osmotic gradient that forces said solubilized agent to diffuse through the rate-controlling membrane at an essentially constant rate into the oral environment, said process comprises:

(a) preparing a pharmaceutically acceptable agent releasing core by blending about 74% w/w of a pharmaceutically acceptable active agent and about 25% w/w of 2-hydroxyethyl methacrylate/methyl methacrylate co-polymer which comprises about 50 mole % of 2-hydroxyethyl methacrylate and about 50 mole % of methyl methacrylate;

(b) granulating the blend in the presence of a solvent mixture consisting of from about 30% v/v of ethyl acetate and about 70% v/v of isopropyl alcohol;

(c) forming uniform granules from the granulated blend and drying off the solvent;

(d) blending the dry granules with talc in a ratio of 99 parts granules and 1 part talc;

(e) compressing the blend into cores; and (f) coating said cores to form said rate-controlling membrane by spraying onto said cores a solution of about 3 to about 5% w/w of a membrane forming 30:70 mole % 2-hydroxyethyl methacrylate/methyl methacrylate co-polymer in a solvent mixture of about 4 parts methylene chloride to about 1 part isopropyl alcohol, wherein said rate-controlling membrane constitutes of from about 8% w/w to about 18% w/w of the total weight of said controlled rate-release device.

12. A process of making a controlled rate-release device capable of releasing fluoride ions at an essentially constant rate into the oral cavity for a period of about thirty to about three hundred twenty days, said controlled ram-release device comprising:

(1) a plurality of granules comprising an intimate blend of 2-hydroxyethyl methacrylate/methyl methacrylate copolymer and said fluoride ions releasing agent, said plurality of granules compressed together to form a core of said device; and (2) an outer layer of a saliva-insoluble, non-erodible rate-controlling membrane encasing said core allowing water to penetrate into said core to solubilize said fluoride ions and allowing the creation of an osmotic gradient that forces said solubilized fluoride ions to diffuse through the rate-controlling membrane at an essentially constant rate into the oral environment, said process comprises:

(a) preparing a fluoride-releasing core by blending about 74% w/w of sodium fluoride and about 25% of 2-hydroxyethyl methacrylate/methyl methacrylate copolymer which comprises about 50 mole % of 2-hydroxyethyl methacrylate and 50 mole % methyl methacrylate;

(b) granulating the blend in the presence of a solvent mixture consisting of about 30% v/v of ethyl acetate and about 70% v/v of isopropyl alcohol;

(c) forming uniform granules from the granulated blend and drying off the solvent;

(d) blending the dry granules with talc in a ratio of 99 parts granules and 1 part talc;

(e) compressing the blend into cores; and (f) coating said cores to form said rate-controlling membrane by spraying onto said cores a solution of about 3 to about 5% w/w of a membrane forming 30:70 mole % 2-hydroxyethyl methacrylate/methyl methacrylate co-polymer in a solvent mixture of about 4 parts methylene chloride to about 1 part isopropyl alcohol, wherein said rate-controlling membrane constitutes of from about 8% w/w to about 18% w/w of the total weight of said controlled rate-release device.

13. The preparative process of claim 12 wherein said coating constitutes from about 10 to about 15% w/w of the total weight of said device.

14. The preparative process of claim 13 wherein said device is capable of releasing about 0.01 to 0.5 mg/day fluoride into the oral cavity upon the action of the saliva.

* * * * *